United States Patent
St. Laurent

(10) Patent No.: US 7,851,650 B2
(45) Date of Patent: Dec. 14, 2010

(54) COMPOUNDS FOR TREATING INFLAMMATION AND PAIN

(75) Inventor: Joseph P. St. Laurent, Lakeville, MA (US)

(73) Assignee: Olatec Industries LLC, Rye Brook, NY (US)

( * ) Notice: Subject to any disclaimer, the term of this patent is extended or adjusted under 35 U.S.C. 154(b) by 0 days.

(21) Appl. No.: 12/725,212

(22) Filed: Mar. 16, 2010

(65) Prior Publication Data

US 2010/0240756 A1    Sep. 23, 2010

Related U.S. Application Data

(60) Provisional application No. 61/161,285, filed on Mar. 18, 2009.

(51) Int. Cl.
  C07C 315/00    (2006.01)
  A01N 37/12    (2006.01)

(52) U.S. Cl. .................................... 562/556; 514/562

(58) Field of Classification Search .................. None
  See application file for complete search history.

(56) References Cited

U.S. PATENT DOCUMENTS 6,706,670 B2    3/2004    Kalota et al.

7,423,064 B2    9/2008    Torrence

OTHER PUBLICATIONS

Strunin et al., Bashkirskii Khimicheskii Zhurnal (2002), 9(1), 39-40, Database Cas No. 2003:123867 [retrieved Oct. 20, 2010] from STN; Columbus, OH, USA.*
Armensto et al., Tetrahedron, 56 (2000) 1103-1109.*
Armesto, X. L. et al., "First Steps in the Oxidation of Sulfur-Containing Amino Acids by Hypohalogenation: Very Fast Generation of Intermediate Sulfenyl Halides and Halosulfonium Cations", Tetrahedron 56 (2000) pp. 1103-1109.
Peskin, Alexander V. et al., "Kinetics of the Reactions of Hypochlorous Acid and Amino Acid Chloramines with Thiols, Methionine, and Ascorbate", Free Radical Biology & Medicine, vol. 30, No. 5, pp. 572-579 (2001).

* cited by examiner

*Primary Examiner*—Karl J Puttlitz
(74) *Attorney, Agent, or Firm*—Howrey LLP; Viola T. Kung

(57) ABSTRACT

The present invention is directed to a compound of 2-N halo-4-methylsulfonyl-butyric acid, such as 2-N chloro-4-methylsulfonyl-butyric acid, or a pharmaceutically acceptable salt or solvate thereof. The present invention is also directed to a pharmaceutical composition comprises the compound and a pharmaceutically acceptable carrier. The present invention is further directed to a method for treating inflammation or inflammatory-related disorders, bacterial infection, pain, or skin conditions, by administering 2-N halo-4-methylsulfonyl-butyric acid to a subject in need thereof.

17 Claims, 2 Drawing Sheets

COMPOUNDS FOR TREATING INFLAMMATION AND PAIN

This application claims priority to U.S. Provisional Application No. 61/161,285, filed Mar. 18, 2009; the content of which is incorporated herein by reference in its entirety.

FIELD OF THE INVENTION

The present invention relates to a novel compound of 2-N halo-4-methylsulfonyl-butyric acid, such as 2-N-chloro-4-methylsulfonyl-butyric acid, and its pharmaceutically acceptable salts. The present invention also relates to methods of using the compound for treating bacterial, viral, fungal diseases; inflammation or inflammatory-related disorders; pain; and skin conditions.

BACKGROUND OF THE INVENTION

The human body is susceptible to many different types of infections from a variety of sources. Viral infection, usually in the form of the common cold, affects virtually everyone each year. While the coughing and sneezing associated with colds may be merely annoying, other common viral infections can be far more serious. Influenza, for example, remains a leading cause of hospitalization and death among Americans.

Bacterial infections such as Staphylococcus infections, account for many serious post-surgical complications. Staphylococcus infection is also the leading culprit in cases of food poisoning, and can be responsible for such life-threatening conditions as Toxic Shock Syndrome (TSS), pneumonia, bone infections (osteomyelitis), mastitis in nursing mothers, endocarditis (infection of the inside of the heart), and bacteremia (blood infection). People who are otherwise healthy typically do not become severely ill from staphylococcus infections, but individuals with weakened immune systems, including the elderly, newborns, and persons with chronic illnesses, such as diabetes, cancer, lung disease, kidney disease, or HIV/AIDS, are at special risk.

Individuals with weakened immune systems are at risk from fungal infections. Fungal infections cause conditions in millions of people in the form of sinus infections, athlete's foot, and yeast infections.

The general term "pain" used herein represents all categories of pain, such as traumatic pain resulting from injury, post surgical pain, inflammatory pain; pain associated with disease such as cancer, AIDS, arthritis, herpes, migraine; pain associated with neuropathy such as diabetic neuropathy, causalgia, brachial plexus avulsion, occipital neuralgia, fibromyalgia, gout, and other forms of neuralgic, neuropathic and idiopathic pain syndromes; pain of varying severity, i.e. mild, moderate and severe pain; acute and chronic pain; and specific organ pain, such as ocular and corneal pain, bone pain, heart pain, skin/burn pain, visceral (kidney, gall bladder, etc.), joint, dental and muscle pain.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

Current therapies of pain include the use of opiod narcotic analgesics such as morphine and fentanyl, nonsteroidal anti-inflammatory drugs (NSAIDS) such as aspirin, ibuprofen and cyclooxygenase inhibitors, or ion channel blockers such as lidocaine and novacaine. These therapies all have limitations, for example, they cause tolerance, dependence, constipation, respiratory depression and sedation (opiods). NSAIDS have gastrointestinal side effects and increase bleeding time, and are not effective in treating severe pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. At the tissue and organ level, inflammation is indicated by pain, swelling, reddening, increased temperature, and loss of function in some cases.

Inflammation is influenced by various exogenous and endogenous agents. Endogenous factors, namely, mediators, antigens, and autogens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Nonsteroidal anti-inflammatory drugs (NSAIDS), such as aspirin, can block certain links of an inflammatory process, but these drugs cannot stabilize damaged cellular membranes, which makes their influence on an inflammatory process limited and insufficient.

There is a need for a composition and a method for treating bacterial, viral, fungal diseases; inflammation or inflammatory-related disorders; pain; and skin conditions. The composition should be economic and easy to manufacture, and the method should be effective and have no significant side effects.

SUMMARY OF THE INVENTION

The present invention is directed to a compound of 2-N halo-4-methylsulfonyl-butyric acid (such as 2-N-chloro-4-methylsulfonyl-butyric acid, 2-N-fluoro-4-methylsulfonyl-butyric acid, and 2-N-bromo-4-methylsulfonyl-butyric acid) or a pharmaceutically acceptable salt or solvate thereof. The present invention is also directed to a pharmaceutical composition comprising the compound and a pharmaceutically acceptable carrier.

The present invention is also directed to a method for treating inflammation or inflammatory-related disorders, bacterial infection, pain, or skin conditions. The method comprises the step of administering 2-N halo-4-methylsulfonyl-butyric acid to a subject in need thereof. The composition comprising the active compound can be applied by any accepted mode of administration including topical, oral, and parenteral (such as intravenous, intramuscular, subcutaneous or rectal). Topical administration and oral administration are preferred.

2-N chloro-4-methylsulfonyl-butyric acid can be prepared by a method comprising the steps of: (a) mixing methionine, a halogenating agent (such as hypochlorite), and a water-immiscible organic solvent and reacting at a temperature between 0-30° C., (b) removing the aqueous phase, and (c) obtaining the compound in the organic solvent.

DETAILED DESCRIPTION OF THE INVENTION

Figure 1A:
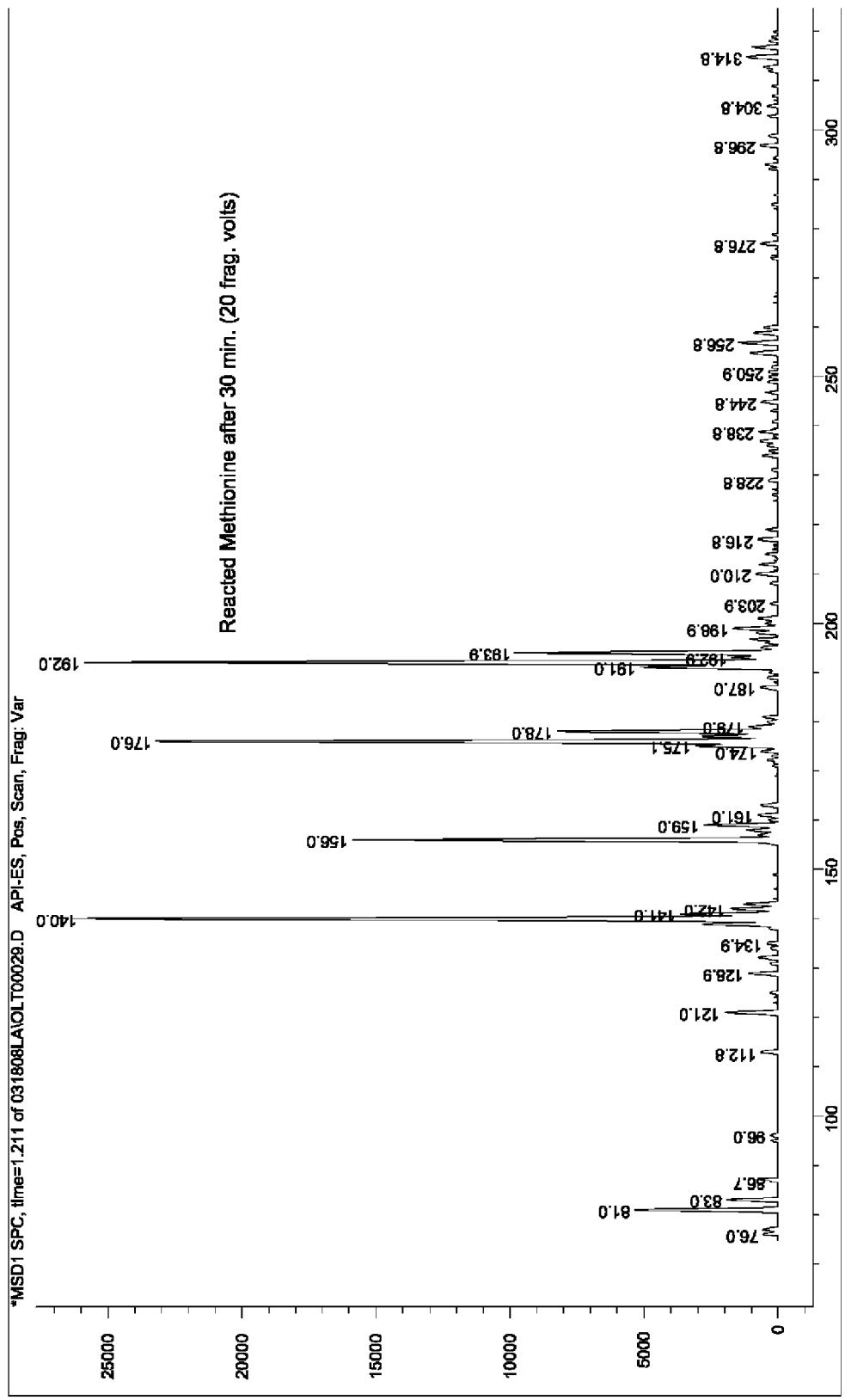
FIG. 1A shows the mass spectra analysis results.

The present invention is directed to a novel compound of 2-N halo-4-methylsulfonyl-butyric acid:

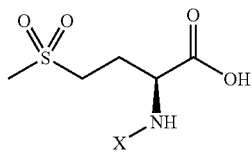

2-N halo-4-methylsulfonyl-butyric acid, where X=F, Cl, or Br.

The present invention is also directed to the pharmaceutically acceptable salts or solvates of 2-N holo-4-methylsulfonyl-butyric acid.

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$ (wherein X is $C_{1-4}$).

"Solvates," as used herein, are addition complexes in which the compound is combined with an acceptable co-solvent in some fixed proportion. Co-solvents include, but are not limited to, ethyl acetate, lauryl lactate, myristyl lactate, cetyl lactate, isopropyl myristate, methanol, ethanol, 1-propanol, isopropanol, 1-butanol, isobutanol, tert-butanol, acetone, methyl ethyl ketone, acetonitrile, benzene, toulene, xylene(s), ethylene glycol, dichloromethane, 1,2-dichloroethane, N-methylformamide, N,N-dimethylformamide, N-methylacetamide, pyridine, dioxane, and diethyl ether.

2-N halo-4-methylsulfonyl-butyric acid can be prepared by a method comprising the steps of: (a) mixing methionine, a water-immiscible organic solvent, and a halogenating agent (such as hypochlorite), and reacting at a temperature between 0-30° C., (b) removing the aqueous phase, and (c) obtaining the compound in the organic solvent.

Methionine can be L-methionine, D-methionine, or a mixture thereof.

Halogenating agents useful for this invention include fluorinating agents, chlorinating agents, and brominating agents. Examples of halogenating agents are hypochlorite, chloramine T, chlorine gas, hydrogen bromide, phosphorus tribromide, phosphorus pentabromide, and 1-chloromethyl-4-fluoro-1, 4-diazoniabicyclo[2.2.2]octane bis-(tetrafluoroborate). A preferred chlorinating agent is hypochlorite (e.g., sodium hypochlorite).

The water-immiscible organic solvent useful in this invention is preferably a semi-polar or non-polar solvent having a polarity of about 0.1-7.5 and protic in nature, such as ethyl acetate, mineral oil, hexane, heptane, methylene chloride, n-butanol, or a fatty acid ester such as lauryl lactate. Preferred organic solvent is ethyl acetate and lauryl lactate.

The reaction of step (a) is carried out at a temperature between 0° C. to ambient temperature, for example 0-35° C., preferably, 0-30° C., and more preferably 0-25° C. The reaction is carried out under basic conditions, for example, between pH 7.1-14, preferably, pH 7.5-7.9.

In one embodiment, methionine is in a solid form and is mixed with a water-immiscible organic solvent and an aqueous halogenating agent. The mixing is optionally carried out under an inert gas, e.g. argon. For example, solid methionine is mixed with a water-immiscible organic solvent first and an aqueous halogenating agent is then added to the rapidly stirred suspension. The reaction time is at least 1 minutes, and is typically from 30 minutes to 24 hours.

In another embodiment, an aqueous solution of a halogenating agent is added to methionine (either in a solid form or an aqueous solution form) and thoroughly mixed. The reaction time is typically between 1 minute to an hour, for example, 2, 5, 10, 15, 30 minutes, or anytime in between (such as 2-30 minutes). The reaction is optionally carried out under an inert gas such as argon. The reactive product 2-N halo-4-methylsulfonyl-butyric acid is not stable in water due to hydrolysis and oxidation. After the methionine/halogenating agent reaction, the reactive product is extracted by the water-immiscible organic solvent.

The mixing of step (a) can be done by any means of mechanical mixing, for example, impeller stirrer, sheer mixing, rotary mixing, etc.

After the reaction of step (a) is complete, the water-organic solvent mixture is allowed to settle. The organic phase is separated from the water phase by any means known to a skilled person such as decanting or pipetting, and the organic solvent extract containing the reactive product 2-N halo-4-methylsulfonyl-butyric acid is obtained. Any non-soluble residues in the organic solvent extract are optionally removed by filtration, decanting, centrifugation, or any means known to a skilled person. The reactive product is stable (without significant oxidation or hydrolysis) in the organic solvent at room temperature (22-28° C.) for at least a month, preferably, 3 months, more preferably 6 months or a year.

In a typical reaction, 1-10 g of methionine, and 20-200 ml of 3-12% (e.g. 6%) hypochlorite are used. In a typical extraction, about 100-1000 ml or more water-immiscible organic solvent is used. The amounts of the above reagents can be scaled up or scaled down.

In one embodiment, the water-immiscible organic solvent is ethyl acetate. After the aqueous phase is removed, the reactive product is optionally further purified by adding a lactate ester solvent or a fatty acid ester solvent to the ethyl acetate solution and mixing, removing the ethyl acetate solvent, and then obtaining the product 2-N chloro-4-methylsulfonyl-butyric acid in the lactate ester solvent or the fatty acid ester solvent. The lactate ester solvent or the fatty acid ester solvent useful in this invention includes, but not limited to, lauryl lactate, myristyl lactate, cetyl lactate, or isopropyl myristate. For example, high purity of lauryl lactate is added to the organic phase and the organic phase is dried in the presence of sodium sulfate. The mixture is filtered to remove the sodium sulfate and the mixture is further distilled using traditional rotary evaporation techniques to remove the ethyl acetate. The resulting solution consists of product 2-N chloro-4-methylsulfonyl-butyric acid in a stabilizing medium of lauryl lactate. The identify of 2-N-Chloro-4-methanesulfonyl-butyric acid is confirmed by infusion mass spectroscopy, Nuclear magnetic resonance spectroscopy (NMR), and can be further characterized by Fourier-transform Infrared spectroscopy (FTIR), ultraviolet spectroscopy (UV), and liquid chromatography mass spectrometry (LC-MS).

Chlorinated hydrocarbons in general are unstable and their half lives are very short (Na and Olson, *Environ Sci Technol*. 41:3220-3225, 2007). Chlorinated alpha amino acids are unstable in water and air, and undergo hydrolytic and oxidation degradation. These unstable properties of chlorinated amino acids appear to be consistent with 2-N halo-4-methylsulfonyl-butyric acid, complicating its isolation and characterization. In addition, the sulfone portion of 2-N halo-4-methylsulfonyl-butyric acid may degrade by reductive mechanisms. The inventors have demonstrated the instability of 2-N halo-4-methylsulfonyl-butyric acid by completing the reaction in an aqueous medium; and immediately (i.e., <5 minutes) initiating flash freezing the reaction solution at −80° C. and subjecting the frozen reaction mixture to lyophilization. Following lyophilization, the material was blanketed with inert gas and hermetically sealed. The resulting product was a white lyocake. Upon exposure to water or air, the white lyocake immediately underwent oxidative degradation and the entire cake turned brick red in color with an off gassing of sulfur like odor.

The inventor has discovered that by including lauryl lactate in the formulation, 2-N halo-4-methylsulfonyl-butyric acid is stabilized because the presence of lauryl lactate protects the compound from its exposure to water. The inventors have discovered that lauryl lactate at about 1-15%, or about 1-5%, or about 5-10%, or about 5-15% (for example, about 10% w/w), provides the needed stability and solubility of 2-N halo-4-methylsulfonyl-butyric acid. "About" as used herein, refers to ±15% of the recited value. Lauryl lactate is considered safe for topical administration. Lauryl lactate is qualified for human use within pharmaceutical and cosmetic products. Preferably lauryl lactate is purified to achieve ≧90%, preferably ≧95% purity; the high purity mitigates the presence of hydrolytic and oxidative agents.

The present invention also provides pharmaceutical compositions comprising one or more pharmaceutically acceptable carrier and 2-N halo-4-methylsulfonyl-butyric acid, or a pharmaceutically acceptable salt, or solvate thereof. The active compound 2-N halo-4-methylsulfonyl-butyric acid in the pharmaceutical compositions in general is in an amount of 0.001-10%, or 0.01-5%, or 0.05-5%, or 0.1-2%, or 0.2-2%, or 0.1-1%, or 0.2-1%, or 0.5-2% (w/w).

The pharmaceutically acceptable carrier can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, hydronium, phosphate, citrate, acetate, and borate; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and polysaccharides such as dextrans, and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

Topical formulations including the active ingredient 2-N halo-4-methylsulfonyl-butyric acid can be in a form of gel, cream, lotion, liquid, emulsion, ointment, spray, solution, and suspension. The inactive ingredients in the topical formulations for example include, but are not limited to, lauryl lactate (emollient/permeation enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

The inventor has discovered that 2-N halo-4-methylsulfonyl-butyric acid, or a pharmaceutically acceptable salt, solvate thereof (the active compound), is useful for treating a variety of diseases or disorders. The active compound can be used as is, or it can be administered in the form of a pharmaceutical composition that additionally contains a pharmaceutically acceptable carrier. In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in the dosage forms such as tablets, capsules, granules, fine granules, powders, syrups, suppositories, injections, or the like. The above pharmaceutical composition can be prepared by conventional methods.

In one embodiment, the present invention provides a method of treating inflammation or inflammatory-related disorders. The term "inflammation" generally refers to a localized reaction of tissue, characterized by the influx of immune cells, which occurs in reaction to injury or infection. The method reduces or alleviates the symptoms associated with inflammation. The present invention preferably provides a method to treat localized manifestations of inflammation characterized by acute or chronic swelling, pain, redness, increased temperature, or loss of function in some cases. The present invention is useful to treat symptomatic inflammation of joints and soft tissues resulting from acute injury or chronic inflammatory disorders including, but not limited to, arthritis (osteoarthritis and rheumatoid arthritis), tendinitis, bursitis, gouty arthritis, polymyalgia rheumatica, and atopic and contact dermatitis.

In another embodiment, the present invention provides a method to alleviate the symptoms of pain regardless of the cause of the pain. The general term "pain" treatable by the present method includes traumatic pain, neuropathic pain, organ pain, and pain associated with diseases. Traumatic pain includes pain resulting from injury, post-surgical pain and inflammatory pain. Neuropathic pain includes neuropathic and idiopathic pain syndromes, and pain associated with neuropathy such as diabetic neuropathy, causalgia, brachial plexus avulsion, occipital neuralgia, fibromyalgia, gout, and other forms of neuralgia. Organ pain includes ocular, corneal, bone, heart, skin/burn, visceral (kidney, gall bladder, etc.), joint, dental and muscle pain. Pain associated with diseases includes pain associated with cancer, AIDS, arthritis, herpes and migraine. The present invention reduces pain of varying severity, i.e. mild, moderate and severe pain; acute and chronic pain. In one embodiment, the present invention is effective in treating pain derived from inflammatory arthritis or degenerative arthritis such as rheumatoid arthritis and osteoarthritis. In another embodiment, the present invention is effective in treating joint pain, muscle pain, tendon pain, and burn pain.

In another embodiment, the present invention provides a method of treating a bacterial disease such as staphylococcus infection.

In another embodiment, the present invention provides a method of treating a viral disease such as influenza infection.

In another embodiment, the present invention provides a method of treating a fungal disease such as athlete's foot, yeast infection, and sinus infection caused by fungus infection.

In another embodiment, the present invention provides a method of treating a skin condition such as skin damages by burns or sun, skin blotches, or wart.

In another embodiment, the present invention provides a method of treating wounds. The wound area half-closure time is improved by the treatment.

The method of the present invention comprises the steps of identifying a subject in need thereof, and administering to the subject an effective amount of 2-N halo-4-methylsulfonyl-butyric acid such as 2-N chloro-4-methylsulfonyl-butyric acid, or a pharmaceutically acceptable salt thereof. "An effective amount," as used herein, is the amount effective to treat a disease by ameliorating the pathological condition or reducing the symptoms of the disease.

The pharmaceutical composition of the present invention can be applied by any of the accepted modes of systemic administration including topical, oral, parenteral (such as intravenous, intramuscular, subcutaneous or rectal), and otherwise systemic routes of administration. The active compound first reaches plasma and then distributes into the target tissues. Dosing of the composition can vary based on the extent of the injury and each patient's individual response. Topical administration and oral administration are preferred routes of administration for the present invention. For systemic administration, plasma concentrations of active compounds delivered can vary according to compounds; but are generally $1 \times 10^{-10}$-$1 \times 10^{-4}$ moles/liter, and preferably $1 \times 10^{-8}$-$1 \times 10^{-5}$ moles/liter.

In a preferred embodiment, the composition is applied topically onto the affected area and rubbed into it. The composition is topically applied at least one or two times a day, preferably 3 to 4 times per day, depending on the medical issue and the disease pathology being chronic or acute. In general, the topical composition comprises about 0.001-1%, preferably about 0.01-1%, or preferably about 0.03-0.3% (w/w), or preferably about 0.05-0.3% of the active compound. For example, the topical composition comprises about 0.05, 0.1, or 0.2% (w/w) of the active compound. Depending on the affected area, typically 1-10 cm$^3$ of the topical composition is applied to the individual per dose. In general, the active compound is applied topically to an individual at 0.05-50, and preferably 0.1-10 mg/dose. The active compound passes through the skin and is delivered to the site of discomfort.

Those of skill in the art will recognize that a wide variety of delivery mechanisms are also suitable for the present invention.

The following examples further illustrate the present invention. These examples are intended merely to be illustrative of the present invention and are not to be construed as being limiting.

EXAMPLES

Example 1

Preparation of Reactive Product

DL-methionine (0.50 g) was weighed into a 125 mL Erlenmeyer flask. Water (25 mL) was added to methionine to give a clear solution. Sodium hypochlorite (CLOROX® bleach, 10 mL) was added to the flask, which was swirled briefly then allowed to stand at room temperature. After 30 min, the solution was transferred to a separatory funnel, and ethyl acetate (50 mL) was added. The mixture was shaken for about 15 min, then, after phase separation, the lower aqueous phase was drained off. CHRYSTAPHYL® (Lauryl lactate, 50 mL) was added to the funnel, and the resultant homogeneous solution was drained into an Erlenmeyer flask containing a large quantity of $Na_2SO_4$. After intermittent swirling for several minutes, the solvents are filtered into a distillation flask, and the ethyl acetate solvent was removed under vacuum ($T_{Bath}$<30° C.). The final volume was reduced to about 50 mL. The resultant product is a semi-viscous clear solution of 2-N chloro-4-methylsulfonyl-butyric acid in lauryl lactate solvent. The clear liquid was transferred to a suitable container and stored at room temperature.

The calculated amount of 2-N chloro-4-methylsulfonyl-butyric acid in lauryl lactate prepared by this example is about 10-15 mg/mL. The calculation is based on an internal standard (see Example 2), and assumes that the ionization responses of the internal standard and 2-N chloro-4-methylsulfonyl-butyric acid are equivalent.

Example 2

Identification of Reactive Product as 2-N Chloro-4-Methylsulfonyl-Butyric Acid

The reactive product of Example 1 was analyzed by infusion mass spectroscopy using methanol as the infusion solvent into a mass spectrometer by electrospray infusion technique.

Equipment and Reagents
  Methanol (HPLC grade or equivalent)
  Ethanol (HPLC grade or equivalent)
  High Performance Liquid Chromatograph (Model HP 1100) or equivalent Mobile Phase Preparation
  In a mobile phase bottle, 750 mL of methanol and 250 mL of ethanol were added and degassed via sonication under vacuum.

Instrument Control (IC) Preparation
  Aliquot portions of Mobile Phase into HPLC vials were used as control samples.

Negative Control (NC) Preparation
  The Negative Control Sample was prepared in a glass vial by mixing a 1 mL aliquot of high purity liquid lauryl lactate (CHRYSTAPHYL®) with 4 mL of Ethyl acetate. The solution was mixed thoroughly and an aliquot was transferred to an amber HPLC analysis vial and hermetically sealed.

System Suitability Standard (SSS)

The System suitability standard was prepared in a glass vial by mixing a 1 mL aliquot of 2-N chloro-4-methylsulfonyl-butyric acid with 4 mL of Ethyl acetate. The solution was mixed thoroughly and an aliquot was transferred to an amber HPLC analysis vial and hermetically sealed.

Internal Standard Stock Solution

The Internal standard (IS=methionine sulfone) was prepared in a suitable volumetric glassware at a concentration of 25 μg/mL in DMSO.

Test Sample (TS)

The test sample was prepared in a glass vial by mixing a 1 mL aliquot of resultant product of Example 1 with 4 mL of Ethyl acetate. Subsequently 10 μL of the IS was added into the test solution. The solution was mixed thoroughly and an aliquot was transferred to an amber HPLC analysis vial and hermetically sealed.

The test sample was analyzed by infusion mass spectroscopy using HPLC-MS-SIM as well as HPLC-MS suing Single Ion Monitoring as well as Total Ion Scan Parameters under the following conditions:

Method Identifier: OLTSIMNL (et al)
Analytical column (where applicable): PHENOMENEX® Luna 5μ Silica (2) 100A
250×4.60 mm 5μ

Figure 1B:
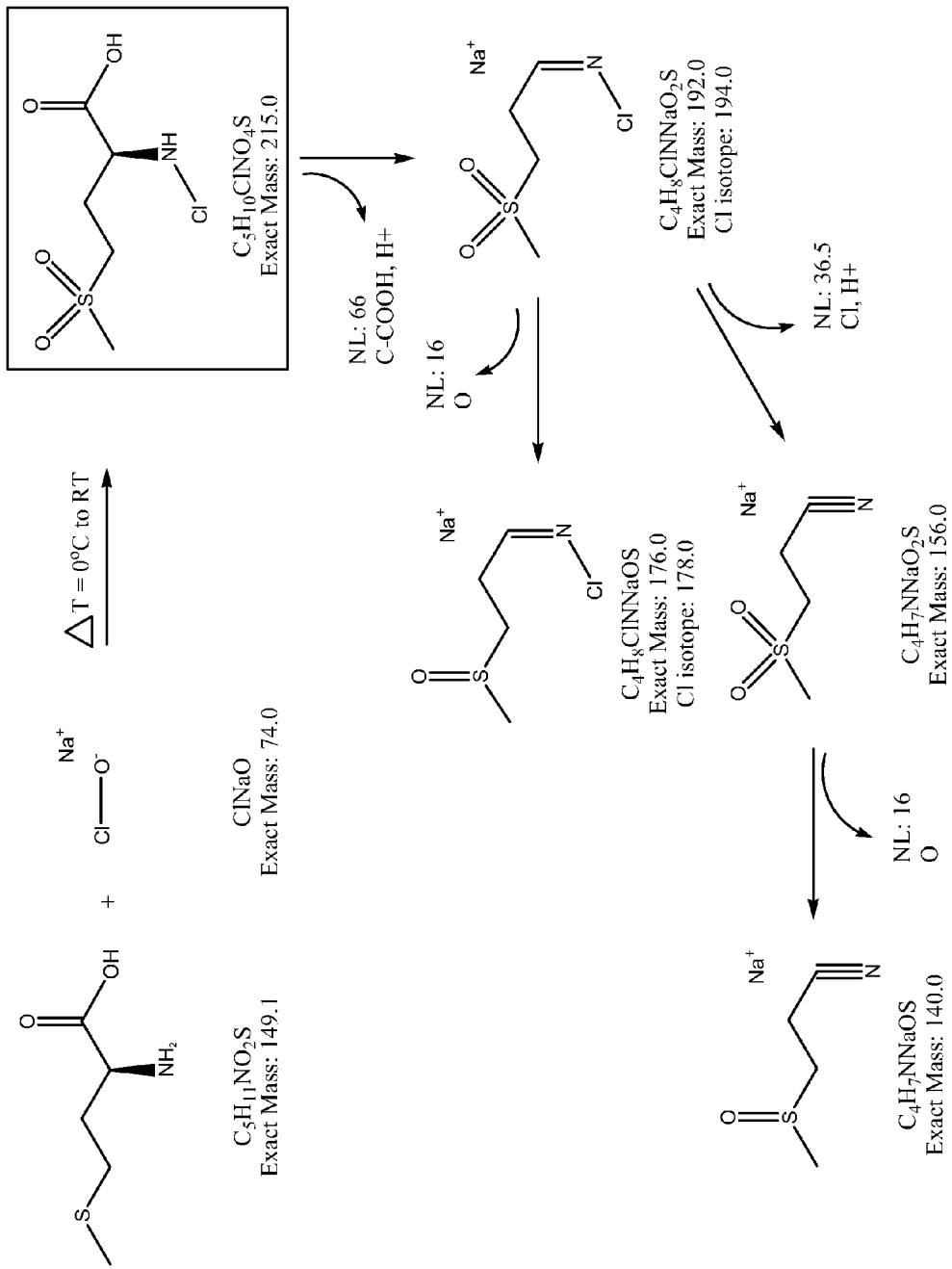
FIG. 1B shows the theoretical fragmentation of 2-N chloro-4-methylsulfonyl-butyric acid.

Total ion spectra were collected from 75 to 375 AMU. The results are shown in FIG. 1. The X-axis shows the mass to charge ratio (directly relevant to the molecular weight) and the Y-axis depicts the intensity of the signal.

The mass spectra analysis of the test sample shows several major ion peaks having a molecular weight of 140, 192, 176, and 156, in the order of decreasing signals. FIG. 1 also shows the theoretical fragmentation of 2-N chloro-4-methylsulfonyl-butyric acid (molecular weight of 215.7), which results in structures having molecular weight of 192, 176, 156, and 140. The isolated fragmentation pattern is resultant of method specific parameters and fragmentation of 2-N chloro-4-methylsulfonyl-butyric acid.

Example 3

Preparation of Reactive Product

DL-Methionine (approximately 1.50 g) was weighed into a 500 mL Erlenmeyer flask containing a stir bar. 150 mL of reagent grade Ethyl Acetate was added to the flask and to the rapidly stirred suspension was added 30 mL of sodium hypochlorite (CLOROX® bleach). The flask was stoppered and stirring was continued at RT for a period of 18 hrs.

The mixture was transferred to a separatory funnel, the aqueous phase was drained off, and 150 mL of high purity lauryl lactate (CHRYSTAPHYL®, Chemic Laboratories) (150 mL) was added to the organic phase. The resultant homogeneous solution was dried in the presence of 20-50 g of sodium sulfate ($Na_2SO_4$), and, after intermittent swirling for several minutes, the solvents were filtered into a distillation flask, which was placed on a Rotavap (T Bath=30-35° C.; 14-18 torr; 2 h) and partially concentrated to remove ethyl acetate. The residual clear liquid (~140 mL) was transferred to a suitable container closure system and stored at room temperature.

Example 4

NMR Results

Uniformly labeled $^{13}C$ Methionine (purity 97-99%) was reacted in D8 Ethyl acetate (EtoAC) (Purity 99.5%) using the procedures described in the first paragraph of Example 3. Approximately 1 g of d8 Ethyl acetate containing an estimated 0.1% u-13C 2-N chloro-4-methylsulfonyl-butyric acid was assessed using $^1H$ NMR at 400 mHz with the sample maintained at 25° C. Additionally the same test sample was assessed using $^{13}C$ NMR @ 100 mHz again with the test sample maintained at 25° C.

Results of the experiment generated the following peaks:
$^1H$ NMR (ETOAC-d8, 400 MHz): 1.78 (1H), 2.56 (β, 2H), 3.42 (α, 2H), 3.93 (α, 1H) $^{13}C$ NMR (EToAC-d8, 100 MHz): δ 18.0, 39.68, 39.77, 48.7, 49.0, 59.0, 171.0

The combined $^1H$ NMR and $^{13}C$ NMR results confirm the sulfone, terminal methyl, and the carboxyl moieties of 2-N-Chloro-4-methanesulfonyl-butyric acid.

Example 5

Anti-Inflammatory Activity of 2-N-Chloro-4-Methylsulfonyl Butyric Acid

Test substances including 2-N chloro-4-methylsulfonyl-butyric acid (active compound, prepared according to Example 1), indomethacin (positive control), and vehicle (lauryl lactate) were evaluated for anti-inflammatory activity in the topical arachidonic acid induced ear swelling model in mice.

Male ICR mice weighing 22±2 g were used in the experiment. Arachidonic acid (2 mg in 20 μL acetone) was applied topically onto the anterior and posterior surfaces of the right ear of test animals. Active compound in vehicle or vehicle (lauryl lactate) was each applied 30 minutes before and 15 minutes after arachidonic acid challenge. Concurrently, the positive control indomethacin in vehicle at 3 mg/ear or vehicle (lauryl lactate) was each applied 30 minutes before and 15 minutes after arachidonic acid. Ear swelling was then measured using a Dyer model micrometer gauge at 60, 90 and 120 minutes after arachidonic acid induction of ear edema as an index of inflammation. Significant activity is defined as a reduction (inhibition) in arachidonic acid induced ear swelling by ≧30% relative to the vehicle-treated group. The results are shown in Table 1.

TABLE 1

| Treatment | Route | Dose | %, ear swelling inhibition after arachidonic acid | | |
|---|---|---|---|---|---|
| | | | 60 min. | 90 min. | 120 min. |
| Lauryl lactate | TOP | 20 μL/ear × 2 | — | — | — |
| Active compound/lauryl lactate | TOP | 2 mg/ear × 2 | 33 | 31 | 34 |
| Indomethacin/lauryl lactate | TOP | 3 mg/ear × 2 | 71 | 65 | 70 |

Based on the results, topical administration of the active compound in lauryl lactate showed significant reduction (33, 31, and 34%) in ear swelling relative to lauryl lactate vehicle group at the 60, 90, and 120 minutes measurement time points after arachidonic acid challenge.

aaa

Example 6

Gel Formulation

The following exemplifies a gel formulation containing 2-N chloro-4-methylsulfonyl-butyric acid (active compound).

| Component | Function | Quantity (% w/w) |
| --- | --- | --- |
| Active compound | Active | 0.05, 0.1 and 0.2% |
| Lauryl lactate | Emollient/Permeation enhancer | 9.95, 10.0 and 10.1% |
| EL-8085 silicone elastomer | Rheology/texture modifier | 65.45% |
| Caprylic/capric triglyceride | Emollient | 8.00% |
| Octisalate | Emollient/UV filter | 5.00% |
| Silicone fluid | Emollient/Diluent | 7.50% |
| Squalene | Emollient | 2.00% |
| Sunflower oil | Emollient | 2.00% |
| Silicone dioxide | Thickening agent | 0.05% |

The gel formulation is prepared by adding the silicone elastomer to a vessel and then adding caprylic/capric triglyceride, octisalate, active compound (in lauryl lactate), silicone fluid, squalene and sunflower oil and blended until homogenous. Silica silylate is added and the batch blended again until homogenous. The gel is then filled in tubes and the tubes capped. The visual appearance of the gel is clear to slightly yellow viscous gel.

Example 7

Treatment of Infections

The resultant product of Example 3 or a gel formulation of Example 6 is applied topically once to three times a day to subjects who exhibit staphylococcal infection. The treatment duration is from 1 week to 3 months. The symptoms of infection are examined after treatment.

Example 8

Treatment of Pain

The resultant product of Example 3 or a gel formulation of Example 6 is applied topically to different subjects having joint pain, arthritic pain, back pain, knee pain, hip pain, bug bite pain, or burn pain. The subjects are evaluated for immediate relief of pain after application of the product.

Example 9

Treatment of Wounds or Injuries

The resultant product of Example 3 or a gel formulation of Example 6 is applied topically once to three times a day to subjects who exhibit burns, sun face blotches, sun damage to skin, or wart. The treatment duration is from 3 days to 3 months. The subjects are evaluated for symptoms after application of the product.

Example 10

Treatment of Wounds in Mice

CD-1 male mice are placed under hexobarbital (90 mg/kg, IP) anesthesia, and the shoulder and back regions of each animal are shaved. A sharp punch (ID 12 mm) is applied to remove the skin including the panniculus carnosus and adherent tissues. 2-N chloro-4-methylsulfonyl-butyric acid in lauryl lactate and lauryl lactate vehicle control are each applied topically immediately following cutaneous injury and then four times daily (at 3-hour intervals) for 10 consecutive days. A positive control mitomycin at 10 μg/mouse and the vehicle control are each administered topically immediately following cutaneous injury and then once daily for 10 consecutive days. The wound area, traced onto clear plastic sheets, is measured by use of an Image—ProPlus (Media Cybernetics, Version 4.5.29) on days 1, 3, 5, 7, 9 and 11. The percent closure of the wound (%) is calculated, and wound half-closure time (CT50) is analyzed by linear regression using Graph-Prism (Graph Software USA).

Example 11

Treatment of Knee Pain

Objectives: To investigate the efficacy of 2-N chloro-4-methylsulfonyl-butyric acid gel in patients with mild to moderate knee pain associated with osteoarthritis following temporary cessation of standard NSAID therapy.

Formulation: The gel formulation contains 2-N chloro-4-methylsulfonyl-butyric acid at 0.1, or 0.2% (Example 6) are used in this example. Placebo contains the same gel without the active compound.

Methodology: A randomized, double-blind, placebo controlled, parallel treatment multicenter Phase 2 clinical activity study.

Patients with painful osteoarthritis of the knee, controlled by a stable dose of standard NSAID therapy for at least 2 months, discontinue use of the NSAIDs for a 7 day washout period. Patients are then randomized in a 1:1:1 ratio (0.1% active gel, 0.2% active gel, placebo). A total of up to 150 patients are enrolled and treated for 7 days with follow-up at 8, 10, 14 and 21 days.

The active Gel or placebo is applied to the affected knee 3 times a day for 7 days for a total of 21 treatments given every 4-6 hours while awake.

Patients are treated for 7 days and followed up for a further 14 days. NSAIDs may be restarted after the Day 10 visit.

Criteria for Evaluation:

Safety:

Adverse Events (AEs) throughout the study.

Physical examination at enrollment (−7 days, start of NSAID washout period), Baseline (Day 1, start of treatment), Day 10 and Day 21.

Vital signs at enrollment (−7 days, start of NSAID washout period), Baseline (Day 1, start of treatment) and Days 2, 4, 8, 10, 14 and 21.

Clinical laboratory measurements at Baseline (Day 1), Day 8 and Day 14.

Clinical Activity:

The primary clinical activity parameters are the measurement of pain at the site of application, as quantified by VAS and the Western Ontario and McMaster University (WOMAC) scale. The effect of treatment on swelling, tenderness and inflammation of the knee is recorded, also the time to reduction or eradication of pain after treatment is recorded.

Study Endpoints:
The primary clinical activity endpoint is:
Change from Baseline (Day 1) to Day 8 in WOMAC functional disability index:
Pain (Scale 0-20).
Stiffness (Scale 0-8).
Physical function (Scale 0-68).
The secondary clinical activity endpoints was:
Change from Baseline (Day 1) to Day 8 in VAS pain scale (1-100).
Within-day change in VAS pain scale on Day 2 and Day 3 as measured by change from daily Baseline (Pre-Treatment 1) to 30 minutes Post Treatment 2.
Change in investigator evaluation of swelling, tenderness and inflammation between Baseline (Day 1) and 30 minutes and 60 minutes after the first application on Day 1.
Change in investigator evaluation of swelling, tenderness and inflammation between Baseline (Day 1) and Day 8.
Time to reduction or eradication of pain subsequent to each topical application of OLT1171 Gel or placebo gel.
Use of rescue medication (APAP).

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A compound of 2-N halo-4-methylsulfonyl-butyric acid or a pharmaceutically acceptable salt or solvate thereof;

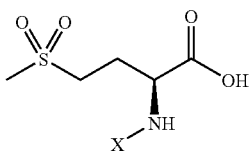

where X=F, Cl, or Br.

2. The compound of claim 1, wherein X=Cl.

3. A pharmaceutical composition comprises the compound of claim 1 and a pharmaceutically acceptable carrier.

4. The pharmaceutical composition according to claim 3, wherein the pharmaceutically acceptable carrier comprises lauryl lactate in an amount of 5-15% (w/w).

5. The pharmaceutical composition according to claim 3, which is in a form of a gel and the compound is in an amount of about 0.03-0.3% (w/w).

6. A method for preparing the compound of claim 1, comprising the steps of:
    (a) mixing methionine, a water-immiscible organic solvent, and a halogenating agent, and reacting at a temperature between 0-30° C.;
    (b) removing the aqueous phase; and
    (c) obtaining the compound in the organic solvent.

7. The method according to claim 6, wherein said water-immiscible organic solvent is ethyl acetate, hexane, heptane, methylene chloride, mineral oil, or a fatty acid ester.

8. The method according to claim 6, wherein said halogenating agent is hypochlorite.

9. The method according to claim 6, wherein the methionine is D-methionine, L-methionine, or a mixture thereof.

10. A method for preparing the compound of claim 2, comprising the steps of:
    (a) mixing methionine, ethyl acetate, and an aqueous hypochlorite solution and reacting at a temperature between 0-30° C.;
    (b) removing the aqueous phase;
    (c) obtaining the compound in ethyl acetate;
    (d) adding a lactate ester solvent or a fatty acid ester solvent to the ethyl acetate solution and mixing;
    (e) removing the ethyl acetate solvent; and
    (f) obtaining the compound in the lactate ester solvent or in the fatty acid ester solvent.

11. The method according to claim 10, wherein said lactate ester solvent is lauryl lactate, myristyl lactate, or cetyl lactate.

12. The method according to claim 10, wherein said fatty acid ester solvent is isopropyl myristate.

13. A method of treating inflammation, comprising the steps of:
    identifying a subject suffering from inflammation, and
    topically administering to the subject the compound of claim 1, in an amount effective to treat inflammation.

14. The method according to claim 13, wherein said method reduces or alleviates the symptoms of localized manifestations of inflammation characterized by acute or chronic swelling, pain, or redness.

15. The method according to claim 13, wherein said inflammation is inflammation of joints or soft tissues.

16. A method of treating pain, comprising the steps of:
    identifying a subject suffering from pain, and
    topically administering to the subject the compound of claim 1, in an amount effective to treat pain.

17. The method according to claim 16, wherein said pain is pain derived from rheumatoid arthritis, pain derived from osteoarthritis, joint pain, muscle pain, tendon pain, or burn pain.

* * * * *